(12) United States Patent
Hasegawa et al.

(10) Patent No.: US 8,830,003 B2
(45) Date of Patent: Sep. 9, 2014

(54) ULTRASONIC GENERATOR AND PROGRAM WRITING METHOD

(75) Inventors: Hiroshi Hasegawa, Hamura (JP); Hiroki Okuzawa, Hamura (JP)

(73) Assignee: Kaijo Corporation, Tokyo (JP)

( * ) Notice: Subject to any disclaimer, the term of this patent is extended or adjusted under 35 U.S.C. 154(b) by 659 days.

(21) Appl. No.: 13/131,337

(22) PCT Filed: Apr. 28, 2009

(86) PCT No.: PCT/JP2009/058366
§ 371 (c)(1),
(2), (4) Date: Jul. 7, 2011

(87) PCT Pub. No.: WO2010/064461
PCT Pub. Date: Jun. 10, 2010

(65) Prior Publication Data
US 2011/0254519 A1    Oct. 20, 2011

(30) Foreign Application Priority Data
Dec. 2, 2008    (JP) .................................. 2008-307510

(51) Int. Cl.
*H03L 7/00* (2006.01)
*B06B 1/02* (2006.01)
*H01L 21/67* (2006.01)
*G01N 29/265* (2006.01)

(52) U.S. Cl.
CPC ............ *B06B 1/0253* (2013.01); *G01N 29/265* (2013.01); *H01L 21/67057* (2013.01); *H01L 21/67253* (2013.01)
USPC ........ 331/34; 73/633; 73/632; 134/1; 134/13; 323/234; 310/334; 702/39; 331/23

(58) Field of Classification Search
CPC ........................................................ A61B 8/00
USPC .............. 331/167, 183, 185, 34, 23; 600/447, 600/437, 443; 154/1, 13; 73/633, 632; 310/334; 702/39
See application file for complete search history.

(56) References Cited

U.S. PATENT DOCUMENTS

| 6,761,690 B2 * | 7/2004 | Sakurai et al. ................ 600/447 |
| 7,022,089 B2 | 4/2006 | Ooba et al. |
| 2002/0057040 A1 | 5/2002 | Shibatani |
| 2002/0177792 A1 | 11/2002 | Ooba et al. |

FOREIGN PATENT DOCUMENTS

| JP | 11-164574 | 6/1999 |
| JP | 2002-112563 | 4/2002 |

(Continued)

OTHER PUBLICATIONS

International Search Report issued Jul. 21, 2009 in International (PCT) Application No. PCT/JP2009/058366.

*Primary Examiner* — Arnold Kinkead
(74) *Attorney, Agent, or Firm* — Wenderoth, Lind & Ponack, L.L.P.

(57) ABSTRACT

An ultrasonic generator is provided, in which the control system can easily be changed in accordance with a cleaning application and a cleaning process. The ultrasonic generator according to the present invention, which causes an ultrasonic transducer to oscillate a signal for ultrasonic vibration, includes a programmable multiple control circuit having a signal generation circuit for generating a signal, and an output adjustment circuit for adjusting the output of the signal from the programmable multiple control circuit, wherein the programmable multiple control circuit has a power control circuit electrically connected to the output adjustment circuit, a phase comparison circuit electrically connected to the output adjustment circuit, a frequency control circuit electrically connected to the phase comparison circuit, and a signal modulation circuit electrically connected to the frequency control circuit via the signal generation circuit.

7 Claims, 8 Drawing Sheets

(56) References Cited

FOREIGN PATENT DOCUMENTS

| JP | 2002-263579 | 9/2002 |
|---|---|---|
| JP | 2002-345915 | 12/2002 |
| JP | 2005-144349 | 6/2005 |
| JP | 2006-78390 | 3/2006 |
| JP | 2006-92211 | 4/2006 |

* cited by examiner

ULTRASONIC GENERATOR AND PROGRAM WRITING METHOD

BACKGROUND OF THE INVENTION

1. Technical Field

The present invention relates to an ultrasonic generator, a program writing method, etc., particularly to an ultrasonic generator having a control system easily changeable in accordance with a cleaning application or a cleaning process, a program writing method, etc.

2. Background Art

Figure 8:
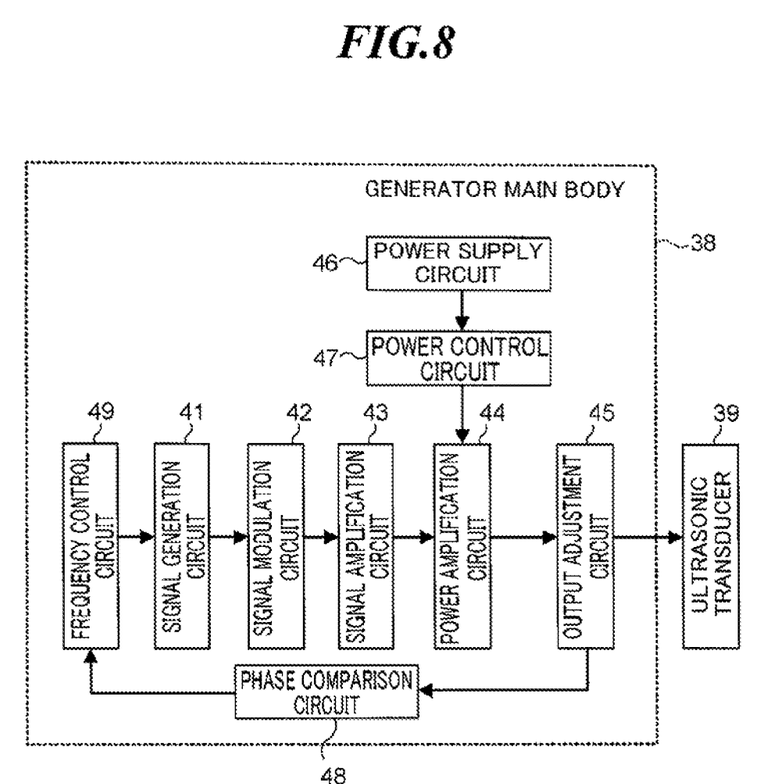
FIG. 8 is a schematic view showing the constitution of a conventional ultrasonic vibration apparatus.

FIG. 8 is a schematic view showing the constitution of a conventional ultrasonic vibration apparatus. The ultrasonic vibration apparatus is one constituting a part of an ultrasonic cleaning machine, and is an apparatus for giving ultrasonic vibration, when cleaning an object to be cleaned (not shown) by using a cleaning fluid (not shown), to the cleaning fluid. The apparatus has a generator main body 38, and an ultrasonic transducer 39 connected to the generator main body 38 by a connector (not shown).

The ultrasonic cleaning machine is a machine for cleaning an object to be cleaned by oscillating a signal for ultrasonic vibration from the generator main body 38, transmitting the signal for ultrasonic vibration to the ultrasonic transducer 39, and giving ultrasonic vibration generated by the ultrasonic transducer 39 to the cleaning fluid.

The generator main body 38 has a signal generation circuit 41, and the signal generator 41 is electrically connected to a signal modulation circuit 42. The signal modulation circuit 42 is electrically connected to a signal amplification circuit 43, and the signal amplification circuit 43 is electrically connected to a power amplification circuit 44. The power amplification circuit 44 is electrically connected to an output adjustment circuit 45, and the output adjustment circuit 45 is electrically connected to a power control circuit 46. The power control circuit 46 is electrically connected to a power supply circuit 47, and the power supply circuit 47 is electrically connected to the power amplification circuit 44.

In addition, the output adjustment circuit 45 is electrically connected to a phase comparison circuit 48, and the phase comparison circuit 48 is electrically connected to a frequency control circuit 49. Moreover, the output adjustment circuit 45 is electrically connected to the ultrasonic transducer 39 via a connector (not shown).

SUMMARY OF THE INVENTION

Meanwhile, for ultrasonic vibration apparatuses, such controls are required as an output power control and an output voltage/current control by the power control circuit 46, a frequency tracking control by the frequency control circuit 49, and the control of the selection of an oscillation system (sine wave, FM modulated wave, burst wave, etc.) by the signal generation circuit 41 and the signal modulation circuit 42. Moreover, for these controls, flexible selection/change is required in accordance with a cleaning application or a cleaning process, and, for these controls, an independent use or a combined use is required.

In conventional ultrasonic vibration apparatuses, the power control circuit 46, the output adjustment circuit 45, the frequency control circuit 49, the signal generation circuit 41, the signal modulation circuit 42 etc. are constituted of ultrasonic transducers such as independent ICs, and thus, in order to realize the aforementioned requirement, it becomes necessary to replace the electronic element or to adjust plural portions of circuits. Since the replacement or the adjustment can not be carried out easily, the realization of the above-described requirement by one kind of ultrasonic vibration apparatus is difficult. Accordingly, users are required to prepare a different ultrasonic vibration apparatus every time when the cleaning application or the cleaning process is to be changed, resulting in spending considerable cost and time. In contrast, manufacturers of ultrasonic vibration apparatuses are always required from users to prepare ultrasonic vibration apparatuses in accordance with the above requirement, and thus, there occurs such problems that the inventory control and the manufacturing line become complex and the manufacturing cost increases.

The present invention has been achieved in consideration of the above situation, and an object of the present invention is to provide an ultrasonic generator, a program writing method etc. capable of changing easily the control system in accordance with the cleaning application or the cleaning process.

In order to solve the problems, the ultrasonic generator according to the present invention is an ultrasonic generator for causing an ultrasonic transducer to oscillate a signal for ultrasonic vibration, and includes:

a programmable multiple control circuit having a signal generation circuit for generating a signal, and an output adjustment circuit for adjusting the output of the signal from the programmable multiple control circuit.

The ultrasonic generator according to the present invention, preferably, further includes a power supply circuit for supplying power to the signal output from the programmable multiple control circuit, and a voltage detection circuit and a current detection circuit for detecting the voltage waveform and the current waveform of the signal output from the output adjustment circuit to the ultrasonic transducer, wherein:

the programmable multiple control circuit has a power control circuit, and the power control circuit detects a voltage effective value, a current effective value and a phase difference from the voltage waveform and the current waveform detected by the voltage detection circuit and the current detection circuit, compares the power presently being output with necessary power, and uses the comparison result to adjust the power supply output from the power supply circuit.

The ultrasonic generator according to the present invention, preferably, further includes a voltage detection circuit and a current detection circuit for detecting the voltage waveform and the current waveform of the signal output from the output adjustment circuit to the ultrasonic transducer, wherein:

the programmable multiple control circuit has a phase comparison circuit and a frequency control circuit, and the phase comparison circuit calculates a phase from the voltage waveform and the current waveform detected by the voltage detection circuit and the current detection circuit, uses the calculated result to estimate the pitch of the frequency presently being output relative to the optimum frequency of the ultrasonic transducer, and uses the estimation result to adjust the frequency of the signal to be generated from the signal generation circuit by the frequency control circuit.

In the ultrasonic generator according to the present invention, preferably, ON/OFF of burst and the parameter of the burst waveform itself are input to the programmable multiple control circuit by an external command, the parameter of the burst waveform is set on the basis of the external command in the programmable multiple control circuit, the reference waveform of the burst is generated, and the generated burst waveform is output to the ultrasonic transducer via the output adjustment circuit.

Furthermore, in the ultrasonic generator according to the present invention, preferably, the programmable multiple control circuit has:

a power control circuit electrically connected to the output adjustment circuit, a phase comparison circuit electrically connected to the output adjustment circuit, a frequency control circuit electrically connected to the phase comparison circuit, and a signal modulation circuit electrically connected to the frequency control circuit via the signal generation circuit.

Moreover, the ultrasonic generator according to the present invention, preferably, further includes a signal amplification circuit for amplifying a signal output from the signal modulation circuit, a power supply circuit for inputting a power to the signal output from the signal amplification circuit, and a power amplification circuit for amplifying the power input from the power supply circuit, wherein:

the power amplification circuit is electrically connected to the output adjustment circuit, and the power control circuit is electrically connected to the power supply circuit.

The program writing method according to the present invention is a method of writing a program into the programmable multiple control circuit in any of aforementioned ultrasonic generators, wherein:

a program is written into the programmable multiple control circuit by connecting an electronic terminal device (for example, a personal computer) to the programmable multiple control circuit and inputting data from the electronic terminal device.

The program writing method according to the present invention is a method of writing a program into the programmable multiple control circuit in any of aforementioned ultrasonic generators, wherein:

the program is written into the programmable multiple control circuit by connecting a recording medium to the programmable multiple control circuit via a sub IC and inputting data from the recording medium via the sub IC.

As described above, according to the present invention, it is possible to provide an ultrasonic generator capable of changing easily the control system in accordance with a cleaning application or a cleaning process, a program writing method, etc.

DETAILED DESCRIPTION OF THE INVENTION

Hereinafter, embodiments of the present invention will be explained with reference to the drawings.

Figure 1A:
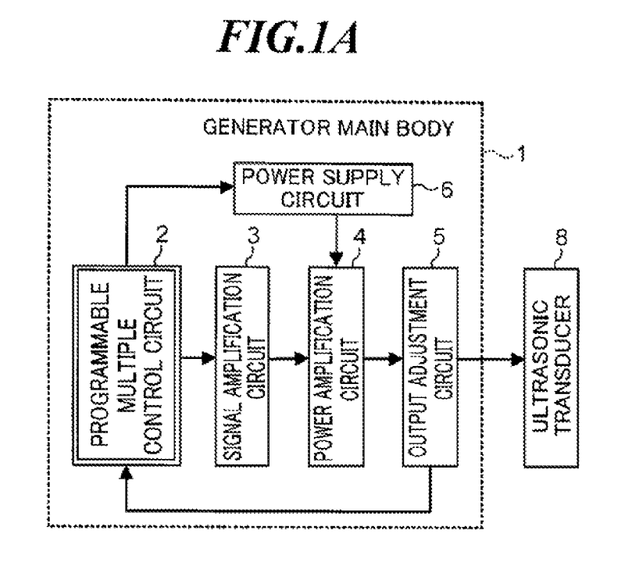
FIG. 1(A) is a schematic view showing the constitution of an ultrasonic vibration apparatus according to an embodiment of the present invention, and (B) is a schematic view showing in detail the constitution of the ultrasonic vibration apparatus shown in (A).
Figure 1B:
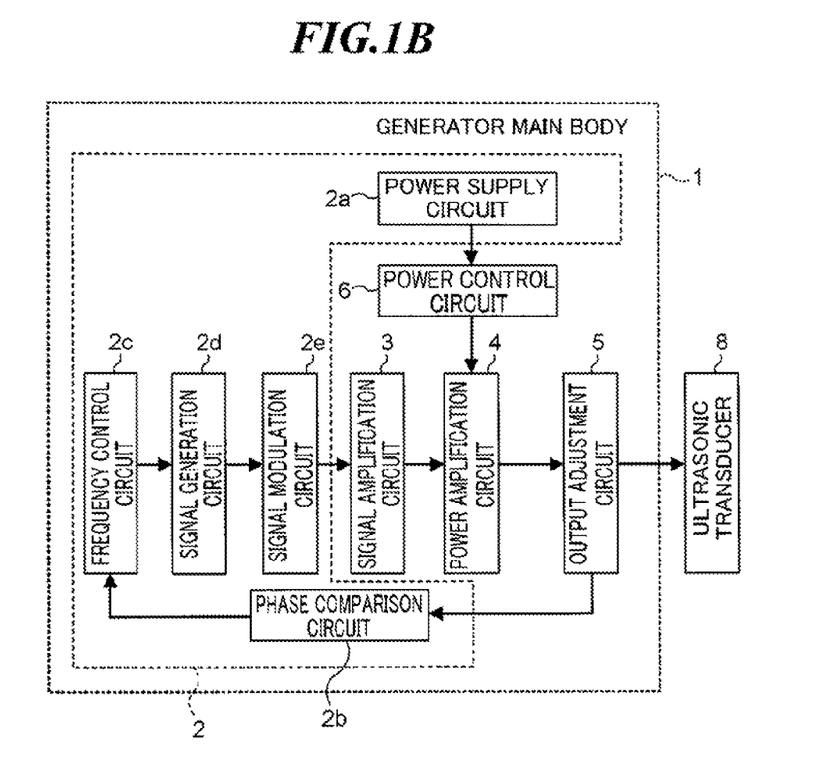

FIG. 1 (A) is a schematic view showing the constitution of an ultrasonic vibration apparatus according to an embodiment of the present invention, and FIG. 1 (B) is a schematic view showing in detail the constitution of the ultrasonic vibration apparatus shown in FIG. 1 (A).

The ultrasonic vibration apparatus shown in FIG. 1 (A) constitutes a part of an ultrasonic cleaning machine, and is an apparatus for giving ultrasonic vibration, when cleaning an object to be cleaned (not shown) by a cleaning fluid (not shown), to the cleaning fluid. The apparatus has a generator main body 1 and an ultrasonic transducer 8 connected to the generator main body 1.

The ultrasonic cleaning machine is an apparatus for cleaning the object to be cleaned by oscillating a signal for ultrasonic vibration from the generator main body 1, transmitting the signal for ultrasonic vibration to the ultrasonic transducer 8, and giving ultrasonic vibration generated by the ultrasonic transducer 8 to the cleaning fluid.

As shown in FIG. 1 (A), the generator main body 1 has a programmable multiple control circuit 2. The programmable multiple control circuit 2 is constituted, for example, of FPGA (field programmable gate array). That is, the programmable multiple control circuit 2 is a circuit formed by writing a program that realizes a function in accordance with an oscillation system or a control system. Accordingly, by previously inputting a function for realizing plural oscillation systems or control systems into the programmable multiple control circuit 2, the selection of an oscillation system or an control system in accordance with a cleaning application or a cleaning process becomes easy. Moreover, it is also easy to write newly another oscillation system or control system into the programmable multiple control circuit 2, the change of the oscillation system or control system in accordance with a cleaning application or cleaning process also becomes easy.

Here, FPGA is also called PLD (programmable logic array), and, as representative characteristics of this kind of IC, there are an SRAM system, an EEPROM system and an antifuse system. The SRAM system is a system in which ON/OFF of a MOS transistor is carried out by the memory content of SRAM cell connected to it, and has such features as volatility and possibility of deletion/rewriting. The EEPROM system has such features as nonvolatility and possibility of deletion/rewriting. The antifuse system is constituted of a switch having properties opposite to the earlier fuse system, in which the switch is in a conduction state before programming and in a non-conduction state after programming, and has such features as nonvolatility and impossibility of deletion/rewriting.

As shown in FIG. 1 (A), the programmable multiple control circuit 2 is electrically connected to the signal amplification circuit 3, and the signal amplification circuit 3 is electrically connected to the power amplification circuit 4. The power amplification circuit 4 is electrically connected to the output adjustment circuit 5, and the output adjustment circuit 5 is electrically connected to the ultrasonic transducer 8. Moreover, the output adjustment circuit 5 is electrically connected to the programmable multiple control circuit 2, and the programmable multiple control circuit 2 is electrically connected to the power supply circuit 6. The power supply circuit 6 is electrically connected to the power amplification circuit 4.

As shown in FIG. 1 (B), the programmable multiple control circuit 2 has a power control circuit 2*a*, a phase comparison circuit 2*b*, a frequency control circuit 2*c*, a signal generation circuit 2*d* and a signal modulation circuit 2*e*. The power control circuit 2*a* is electrically connected to the power supply circuit 6 and the output adjustment circuit 5, respectively, and power supply circuit 6 is electrically connected to the power amplification circuit 4. In addition, the output adjustment circuit 5 has a current detection circuit (not shown) and a voltage detection circuit (not shown) for detecting the current and the voltage of a signal output to the ultrasonic transducer 8.

The output adjustment circuit 5 is electrically connected to the phase comparison circuit 2*b*. The phase comparison circuit 2*b* is electrically connected to the frequency control circuit 2*c*, and the frequency control circuit 2*c* is electrically connected to the signal generation circuit 2*d*. The signal generation circuit 2*d* is electrically connected to the signal modulation circuit 2*e*, and the signal modulation circuit 2*e* is electrically connected to the signal amplification circuit 3.

The ultrasonic vibration apparatus shown in FIG. 1 (B) is constituted so that: the frequency is controlled by the frequency control circuit 2*c*, a signal having a prescribed frequency is generated by the signal generation circuit 2*d*, the signal is modulated by the signal modulation circuit 2*e* and is amplified by the signal amplification circuit 3, the amplified signal is input to the power amplification circuit 4 and the power is controlled by the power control circuit 2*a*, the power is input to the power amplification circuit 4 by the power supply circuit 6 and is amplified by the power amplification circuit 4, and the signal for ultrasonic vibration output-adjusted by the output adjustment circuit 5 is output to the ultrasonic transducer 8. Furthermore, the ultrasonic vibration apparatus is constituted so that the current and the voltage of the signal for ultrasonic vibration output-adjusted by the output adjustment circuit 5 is detected by the current detection circuit and the voltage detection circuit, the phase is compared by the phase comparison circuit 2*b*, and the comparison result is input to the frequency control circuit 2*c*.

The power control circuit 2*a* has a function of controlling the output power, and of controlling the output voltage/current. The current detection circuit, the voltage detection circuit, the phase comparison circuit 2*b* and the frequency control circuit 2*c* have a function of carrying out the frequency tracking control. The signal generation circuit 2*d* and the signal modulation circuit 2*e* have a function of controlling the selection of the oscillation system (sine wave, FM modulated wave, burst wave, etc.). Details of these controls will be explained by using FIGS. 2 to 4.

Figure 2:
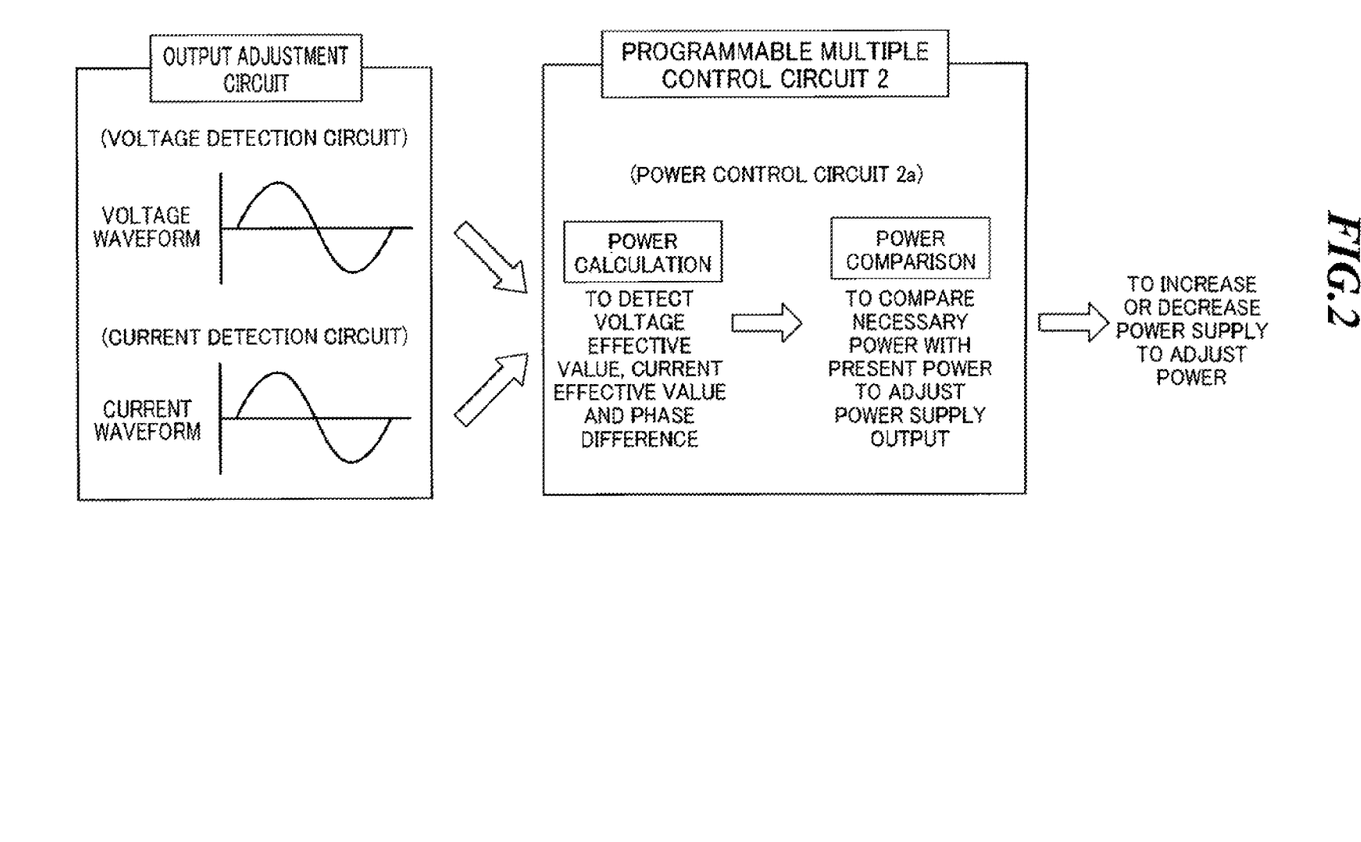
FIG. 2 is a drawing for explaining a method of carrying out a power control in the ultrasonic vibration apparatus shown in FIG. 1.

FIG. 2 is a drawing for explaining the method of carrying out a power control in the ultrasonic vibration apparatus shown in FIG. 1.

The cleaning power when the ultrasonic vibration is given to a cleaning fluid in a cleaning bath by the ultrasonic transducer 8 relates to the power output from the generator main body 1, and when the power fluctuates, the cleaning power of ultrasonic wave also fluctuates. Accordingly, by controlling the output power of the generator main body 1, it becomes possible to control the cleaning power of ultrasonic wave in the cleaning bath.

The voltage detection circuit and the current detection circuit detect the voltage waveform and the current waveform of the signal output from the output adjustment circuit 5 of the generator main body 1 to the ultrasonic transducer 8, and the detected voltage waveform and the current waveform are input to the power control circuit 2*a* of the programmable multiple control circuit 2. The power control circuit 2*a* detects the voltage effective value, the current effective value and the phase difference, and compares the power presently output with a preset power. The comparison result is used to adjust the power supply output from the power supply circuit 6, and thus, the ultrasonic generator is adjusted so that the preset power is supplied. In this way, the power is controlled.

Figure 3:
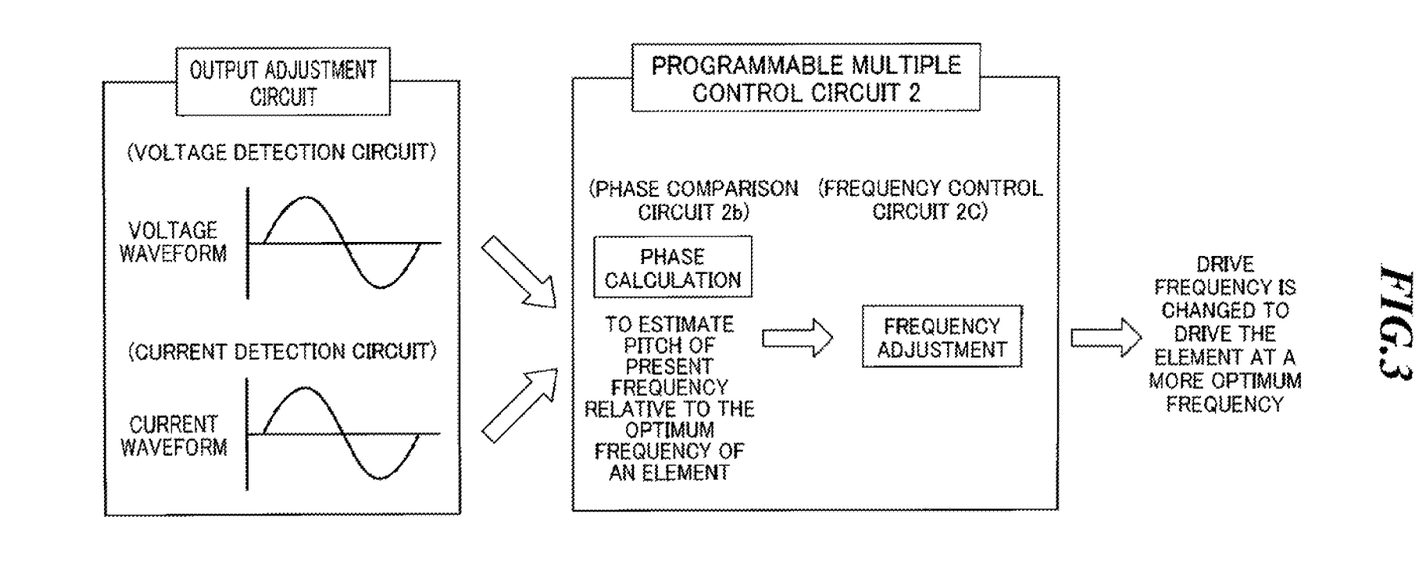
FIG. 3 is a drawing for explaining a method of carrying out a frequency tracking control in the ultrasonic vibration apparatus shown in FIG. 1.

FIG. 3 is a drawing for explaining the method of carrying out the frequency tracking control in the ultrasonic vibration apparatus shown in FIG. 1.

In the ultrasonic transducer 8 that outputs an ultrasonic wave, the optimum frequency that gives the highest efficiency of the ultrasonic output varies depending on the power to be input or temperature. That is, by detecting the optimum frequency and driving the ultrasonic transducer 8 at the optimum frequency, it becomes possible to output effectively the ultrasonic wave.

The voltage detection circuit and the current detection circuit detect the voltage waveform and the current waveform of the signal output from the output adjustment circuit 5 of the generator main body 1 to the ultrasonic transducer 8, and the detected voltage waveform and the current waveform are input to the phase comparison circuit 2*b* of the programmable multiple control circuit 2. The phase comparison circuit 2*b* calculates the phase, and estimates the level of the frequency presently being output, relative to the optimum frequency of the ultrasonic transducer 8. The estimation result is used to adjust the frequency by the frequency control circuit 2*c*. In this way, the frequency tracking control is carried out in which the drive frequency of the ultrasonic transducer 8 is changed to thereby drive the ultrasonic transducer at a more appropriate frequency.

Figure 4:
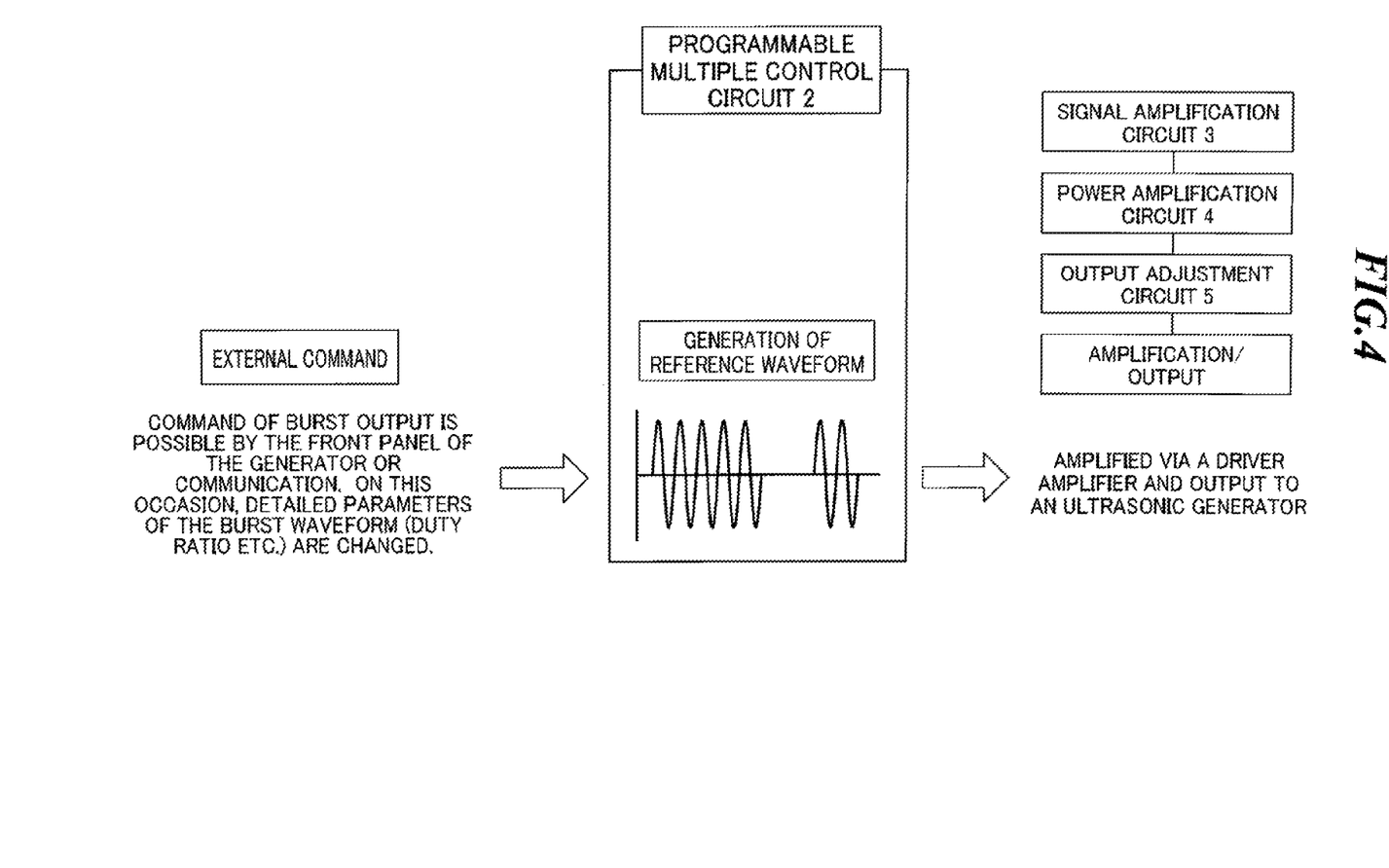
FIG. 4 is a drawing for explaining a method of carrying out a burst output in the ultrasonic vibration apparatus shown in FIG. 1.

FIG. 4 is a drawing for explaining a method of carrying out a burst output in the ultrasonic vibration apparatus shown in FIG. 1.

Depending on the ultrasonic wave cleaning, a state in which an ultrasonic wave is continuously output generates significantly a standing wave due to the ultrasonic wave in a cleaning bath, which results in the occurrence of cleaning unevenness. Consequently, the output of a burst signal from the ultrasonic transducer 8 can reduce the formation of the standing waves, and thus, the cleaning unevenness can be reduced. The optimum burst waveform on this occasion varies depending on an ultrasonic wave frequency or a cleaning process, and thus, preferably a wide range of burst waveform is previously set in the programmable multiple control circuit 2.

ON/OFF of the burst and the parameter of the burst waveform itself are input to the programmable multiple control circuit 2 by a front control panel (not shown) of the generator main body 1, communication, or the like. The programmable multiple control circuit 2 sets detailed parameters (duty ratio etc.) of the burst waveform on the basis of the input command to thereby generate the reference waveform of the burst. The generated burst waveform is amplified via the signal amplification circuit 3, the power amplification circuit 4 and the output adjustment circuit 5, which is output to the ultrasonic transducer 8. Meanwhile, the reference waveform is generated in each case, and thus, it is not necessary to store the reference waveform in a memory. That is, the use of the programmable multiple control circuit 2 makes it possible to set a wide range of burst waveform.

Figure 5:
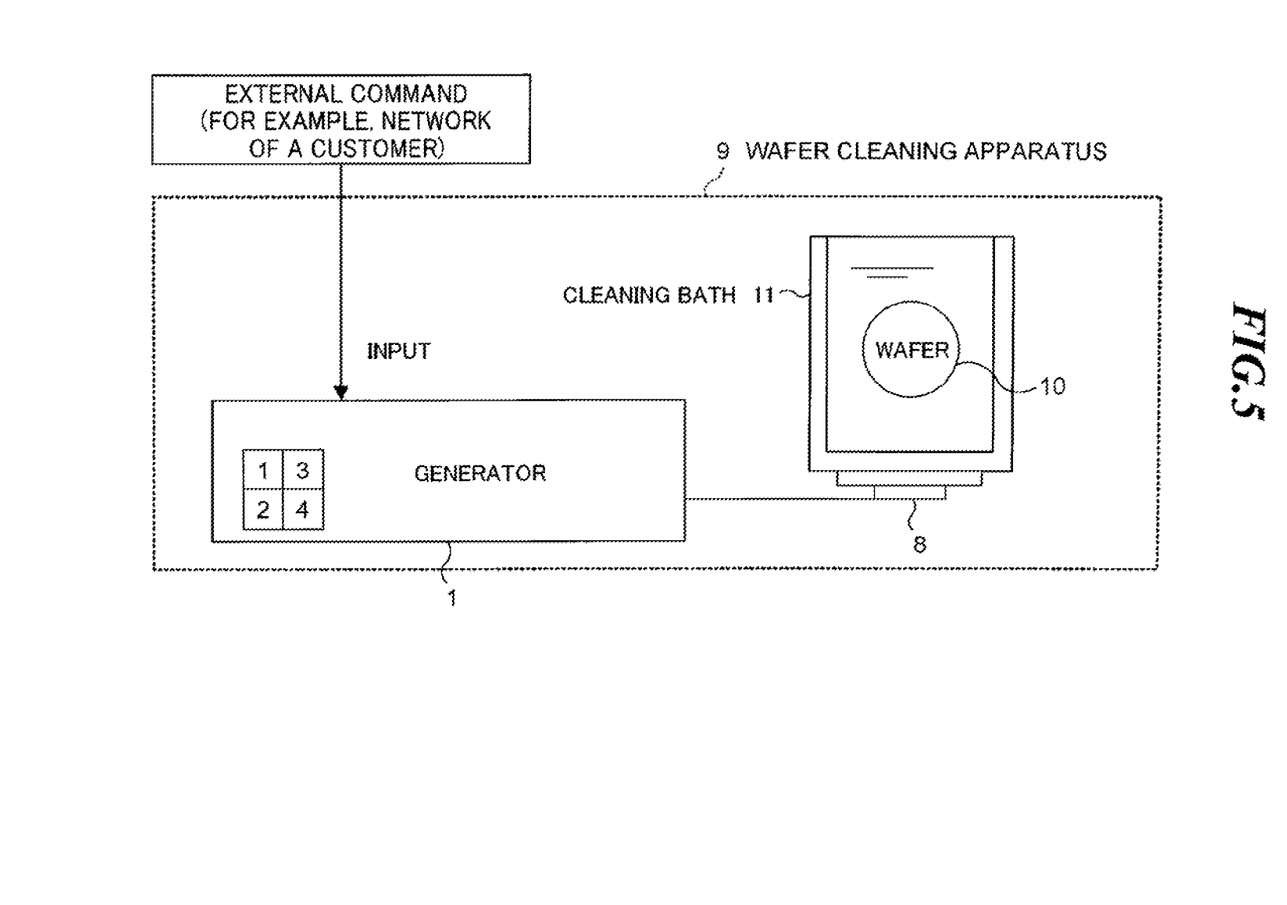
FIG. 5 is a schematic view showing a whole constitution of a wafer cleaning apparatus carrying out the control shown in FIGS. 2 to 4.

FIG. 5 is a schematic view showing the whole constitution of a wafer cleaning apparatus carrying out the control shown in FIGS. 2 to 4.

The wafer cleaning apparatus 9 is an apparatus for carrying out the ultrasonic wave cleaning for a wafer 10, and has the generator main body 1, the ultrasonic transducer 8, and the cleaning bath 11 containing a cleaning fluid to which an ultrasonic wave is output from the ultrasonic transducer 8.

In the wafer cleaning apparatus 9, the recipe of an ultrasonic wave cleaning by an external command (for example, an external command using a network of a customer) is input to the generator main body 1 by communication etc., and on the basis of the input command, the ultrasonic wave cleaning of a wafer is carried out while carrying out any one of controls in FIGS. 2 to 4 or the control by the combination of these in accordance with the recipe mode (cleaning mode) of the wafer cleaning apparatus.

That is, the generator main body 1 shown in FIG. 5 has cleaning modes 1 to 3, in which the cleaning mode 1 is the power control mode shown in FIG. 2, the cleaning mode 2 is the frequency tracking control mode shown in FIG. 3, and the cleaning mode 3 is the output control mode of the burst waveform. The signal of the recipe communication corresponding to the single cleaning mode or the cleaning mode obtained by combining these is input to the generator main body, and on the basis of the input command, the ultrasonic wave cleaning of a wafer is carried out. The generator main body 1 may, for example, carry out the control of the single cleaning mode, carry out the frequency tracking control of the cleaning mode 2 while carrying out the power control of the cleaning mode 1, carry out the burst waveform output control of the cleaning mode 3 while carrying out the frequency tracking control of the cleaning mode 2, or carry out the frequency tracking control of the cleaning mode 2 and the power control of the cleaning mode 1 while carrying out the output control of the burst waveform of the cleaning mode 3. Furthermore, the free addition of cleaning modes to the generator main body 1 makes a more thorough cleaning possible.

Meanwhile, through the attachment of a barcode to a wafer that is an object to be cleaned, or a carrier for carrying it, and through reading the barcode, the cleaning mode may be input to the generator main body of the wafer cleaning apparatus 9.

In the above-described ultrasonic vibration apparatus, the power control circuit 2a carrying out the control of the output power and the control of the output voltage/current, the phase comparison circuit 2b and the frequency control circuit 2c carrying out the frequency tracking control etc., and the signal generation circuit 2d and the signal modulation circuit 2e carrying out the control of the selection of the oscillation system (sine wave, FM modulated wave, burst wave, etc.) are put together in the programmable multiple control circuit 2. Consequently, it becomes possible to change considerably the control system by rewriting the program of the programmable multiple control circuit 2, and at the same time, it becomes easy to carry out controls that are complex as compared with conventional ones, such as the combination of control systems, the change of priority of controls, the change of respective control accuracies, etc. Accordingly, options of the method of controlling the generator can be increased in the ultrasonic wave cleaning, and the execution of a new cleaning recipe also becomes possible.

Moreover, various generator main bodies can be realized by rewriting the program of the programmable multiple control circuit 2, and thus, the generator main body can be made common. Accordingly, there is such advantage that a user needs not to prepare another ultrasonic vibration apparatus every time when the user changes the cleaning application or the cleaning process and can reduce considerably the cost and time, and such advantage that a manufacturer of ultrasonic vibration apparatuses needs not to prepare plural kinds of ultrasonic vibration apparatuses and can simplify the inventory control and manufacturing line to thereby reduce the manufacturing cost.

Moreover, the generator main body 1 has the programmable multiple control circuit 2. Consequently, in the case where the frequency of the ultrasonic wave is to be changed by the change of the cleaning recipe, when replacing the ultrasonic transducer being used with an ultrasonic transducer having a frequency different from that thereof, it becomes possible to change easily the frequency by rewriting the program of the frequency control circuit 2c, the signal generation circuit 2d etc. of the programmable multiple control circuit 2. This means that the difference in control methods, caused by the difference in ultrasonic wave frequencies can be covered by the generator main body 1 of the present embodiment, and that communizing the generator main body can be realized.

Particularly, ultrasonic transducers have electric properties that differ largely according to the shape and frequency thereof, and thus, for every kind of ultrasonic transducers, the drive circuit of the generator main body 1 is required to be changed considerably. But, by rewriting the program of the programmable multiple control circuit 2, the internal circuit thereof can be changed considerably. Accordingly, the replacement of the generator main body 1 is not needed, and thus replacement of the ultrasonic transducer with one having a different frequency. In other words, the generator main body can also be communized with respect to different ultrasonic wave frequencies.

Moreover, in the case where the ultrasonic transducer 8 breaks down, when the broken-down ultrasonic transducer is to be replaced with another ultrasonic transducer having the same frequency, countermeasures are possible by the program of the frequency control circuit 2c, the signal generation circuit 2d etc. of the programmable multiple control circuit 2.

Particularly, the programmable multiple control circuit 2 contains the circuit for which the adjustment is required, when the ultrasonic transducer is replaced, because of the existence of the variation in electric properties according to the individual difference thereof even if the kind of the ultrasonic transducer 8 is the same. Accordingly, when replacing the broken-down ultrasonic transducer 8 with another ultrasonic transducer, countermeasures are possible by the program of the programmable multiple control circuit 2, without replacing the generator main body 1.

Figure 6:
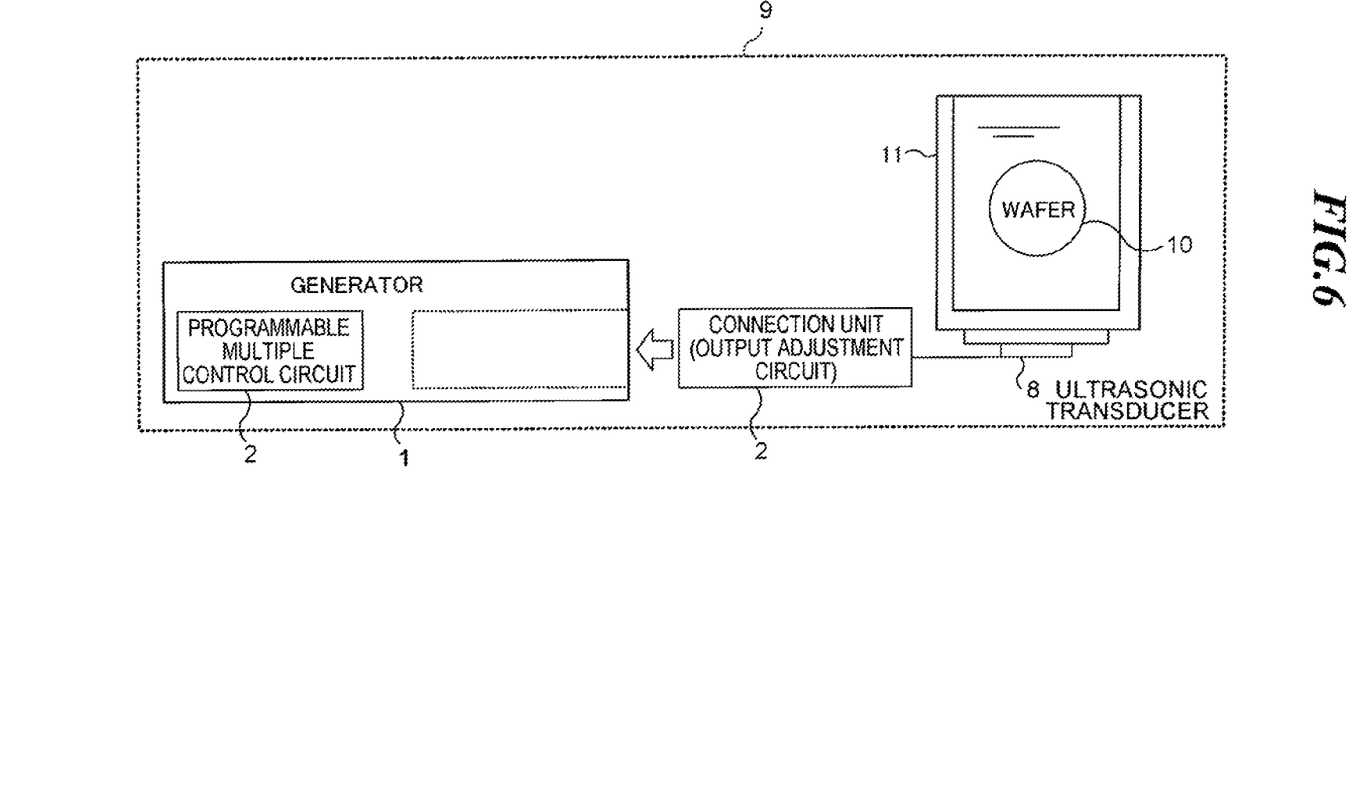
FIG. 6 is a schematic view showing another example of the whole constitution of the wafer cleaning apparatus shown in FIG. 5.

FIG. 6 is a schematic view showing another example of the whole constitution of the wafer cleaning apparatus shown in FIG. 5, in which the same symbol is given to the same part in FIG. 5 and only different parts are explained.

A connection unit 5a has a similar function as the output adjustment circuit shown in FIG. 1, and is constituted attachably/detachably to the generator main body 1. The connection unit 5a is electrically connected to the ultrasonic transducer 8.

The wafer cleaning apparatus shown in FIG. 6 can also produce a similar effect as that of the wafer cleaning apparatus shown in FIG. 5.

Moreover, in the wafer cleaning apparatus shown in FIG. 6, the connection unit 5a is made attachable and detachable, and thus, various kinds (for example, frequency, shape, etc.) of ultrasonic transducers can be used without modifying the output adjustment circuit within the generator. That is, by reserving the ultrasonic transducer 8 and plural sets of connection units 5a corresponding to the kind thereof, one ultrasonic transducer can be used by simply replacing the connection unit 5a with another one and by being changed to another kind of ultrasonic transducer without changing the generator main body 1. Furthermore, by inputting a program to the programmable multiple control circuit 2 so as to carry out the optimum control for the ultrasonic transducer, it becomes possible to carry out more ideal ultrasonic wave cleaning.

Figure 7A:
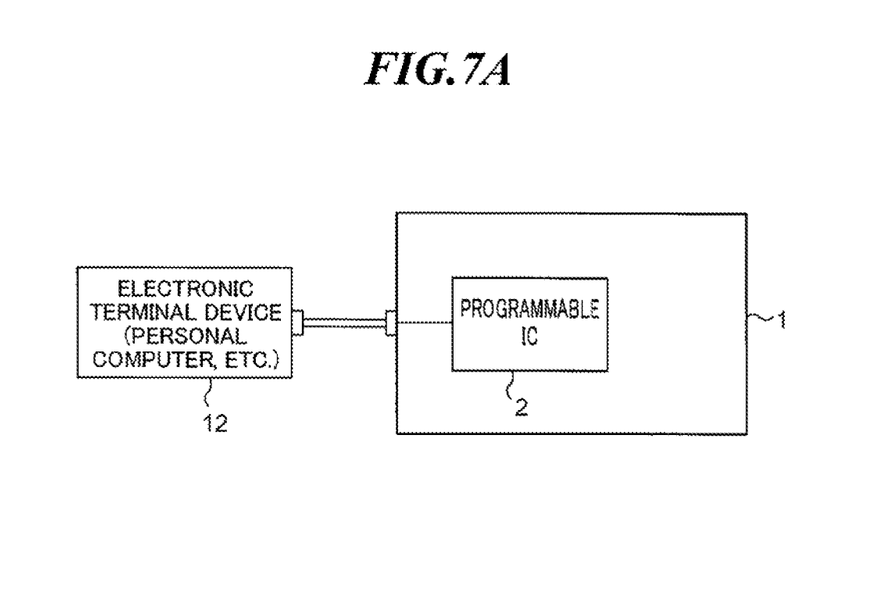
FIG. 7(A) is a drawing for explaining a method of rewriting the program of the programmable multiple control circuit shown in FIG. 1, and (B) is a drawing showing a modification of the method shown in FIG. 7(A).

FIG. 7(A) is a drawing for explaining a method of rewriting the program of the programmable multiple control circuit shown in FIG. 1. The program can be rewritten easily in an extremely short time by connecting the electronic terminal device (for example, a personal computer PC etc.) 12 to the programmable multiple control circuit 2 of the generator main body 1 and transferring data from the electronic terminal device 12.

Figure 7B:
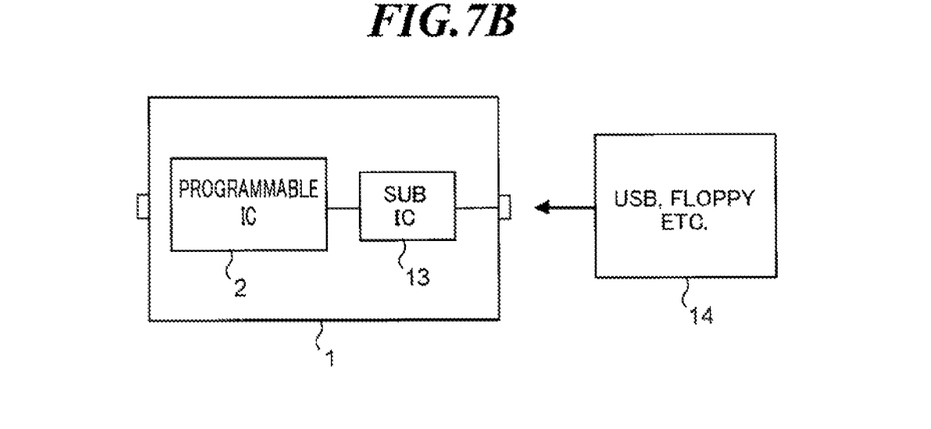

FIG. 7(B) is a drawing showing a modification of the method shown in FIG. 7(A). To the generator main body 1, a sub IC 13 is arranged, and the sub IC 13 is electrically connected to the programmable multiple control circuit 2. To the sub IC 13, a recording medium such as USB or floppy (registered trade mark) is connected, and by transferring data from the recording medium to the programmable multiple control circuit 2 via the sub IC 13, the program can be rewritten easily and in an extremely short time.

Meanwhile, the present invention is not limited to the above-described embodiments, but can be practiced after various changes within a range not deviating from the gist of the present invention. For example, in the above-described embodiment, the programmable multiple control circuit 2 is constituted as shown in FIG. 1(B), but the constitution is an example of the programmable multiple control circuit, and another constitution is also possible.

DESCRIPTION OF REFERENCE NUMERALS AND SYMBOLS

1 . . . generator main body
2 . . . programmable multiple control circuit
2a . . . power control circuit
2b . . . phase comparison circuit
2c . . . frequency control circuit
2d . . . signal generation circuit
2e . . . signal modulation circuit
3 . . . signal amplification circuit
4 . . . power amplification circuit
5 . . . output adjustment circuit
5a . . . connection unit (output adjustment circuit)
6 . . . power supply circuit
8 . . . ultrasonic transducer
9 . . . wafer cleaning apparatus
10 . . . wafer
11 . . . cleaning bath
12 . . . electronic terminal device
13 . . . sub IC
14 . . . recording medium such as USB or floppy (registered trade mark)

The invention claimed is:
1. An ultrasonic cleaning apparatus, comprising:
a cleaning fluid for cleaning an object to be cleaned;
an ultrasonic transducer for applying an ultrasonic vibration to the cleaning fluid; and
an ultrasonic generator causing the ultrasonic transducer to oscillate a signal for ultrasonic vibration, wherein
the ultrasonic generator comprises:
a programmable multiple control circuit having a signal generation circuit for generating a signal,
an output adjustment circuit for adjusting the output of the signal from the programmable multiple control circuit,
a power supply circuit for supplying power to the signal output from the programmable multiple control circuit,
a voltage detection circuit and a current detection circuit for detecting the voltage waveform and the current waveform of the signal output from the output adjustment circuit to the ultrasonic transducer, wherein
the programmable multiple control circuit has a power control circuit, and
the power control circuit detects a voltage effective value, a current effective value and a phase difference from the voltage waveform and the current waveform detected by the voltage detection circuit and the current detection circuit, compares the power presently being output with necessary power, and uses the comparison result to adjust the power supply output from the power supply circuit.

2. An ultrasonic cleaning apparatus, comprising:
a cleaning fluid for cleaning an object to be cleaned;
an ultrasonic transducer for applying an ultrasonic vibration to the cleaning fluid; and
an ultrasonic generator causing the ultrasonic transducer to oscillate a signal for ultrasonic vibration, wherein
the ultrasonic generator comprises:
a programmable multiple control circuit having a signal generation circuit for generating a signal,
an output adjustment circuit for adjusting the output of the signal from the programmable multiple control circuit,
a voltage detection circuit and a current detection circuit for detecting the voltage waveform and the current waveform of the signal output from the output adjustment circuit to the ultrasonic transducer, wherein
the programmable multiple control circuit has a phase comparison circuit and a frequency control circuit, and
the phase comparison circuit calculates a phase from the voltage waveform and the current waveform detected by the voltage detection circuit and the current detection circuit, uses the calculated result to estimate the pitch of the frequency presently being output relative to the optimum frequency of the ultrasonic transducer, and uses the estimation result to adjust the frequency of the signal to be generated from the signal generation circuit by the frequency control circuit.

3. An ultrasonic cleaning apparatus, comprising:
a cleaning fluid for cleaning an object to be cleaned,
an ultrasonic transducer for applying ultrasonic vibration to the cleaning fluid; and
an ultrasonic generator causing the ultrasonic transducer to oscillate a signal for ultrasonic vibration, wherein
the ultrasonic generator comprises:
a programmable multiple control circuit having a signal generation circuit for generating a signal, and
an output adjustment circuit for adjusting the output of the signal from the programmable multiple control circuit, wherein
ON/OFF of burst and the parameter of the burst waveform itself are input to the programmable multiple control circuit by an external command, the parameter of the burst waveform is set on the basis of the external command in the programmable multiple control circuit, the reference waveform of the burst is generated, and the generated burst waveform is output to the ultrasonic transducer via the output adjustment circuit.

4. An ultrasonic cleaning apparatus, comprising:
a cleaning fluid for cleaning an object to be cleaned;
an ultrasonic transducer for applying ultrasonic vibration to the cleaning fluid; and
an ultrasonic generator causing the ultrasonic transducer to oscillate a signal for ultrasonic vibration, wherein
the ultrasonic generator comprises:
a programmable multiple control circuit having a signal generation circuit for generating a signal, and
an output adjustment circuit for adjusting the output of the signal from the programmable multiple control circuit, wherein
the programmable multiple control circuit comprises:
a power control circuit electrically connected to the output adjustment circuit,
a phase comparison circuit electrically connected to the output adjustment circuit,
a frequency control circuit electrically connected to the phase comparison circuit, and
a signal modulation circuit electrically connected to the frequency control circuit via the signal generation circuit.

5. The ultrasonic cleaning apparatus according to claim 4, wherein the ultrasonic generator further comprises a signal amplification circuit for amplifying a signal output from the signal modulation circuit, a power supply circuit for inputting a power to the signal output from the signal amplification circuit, and a power amplification circuit for amplifying the power input from the power supply circuit, wherein:
the power amplification circuit is electrically connected to the output adjustment circuit, and
the power control circuit is electrically connected to the power supply circuit.

6. The ultrasonic cleaning apparatus of any one of claims 1 to 4, wherein a program is written into the programmable multiple control circuit,
the program being written into the programmable multiple control circuit by connecting an electronic terminal device to the programmable multiple control circuit and inputting data from the electronic terminal device.

7. The ultrasonic cleaning apparatus of any one of claims 1 to 4, wherein a program is written into the programmable multiple control circuit,
the program being written into the programmable multiple control circuit by connecting a recording medium to the programmable multiple control circuit via a sub IC and inputting data from the recording medium via the sub IC.

* * * * *